United States Patent
Highsmith et al.

(10) Patent No.: US 12,268,413 B2
(45) Date of Patent: Apr. 8, 2025

(54) RECOMMENDING TRANSSEPTAL NEEDLE CURVATURE BASED ON ANATOMY

(71) Applicant: Biosense Webster (Israel) Ltd., Yokneam (IL)

(72) Inventors: Debby Highsmith, Irvine, CA (US); Joaquin Kurz, Irvine, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 146 days.

(21) Appl. No.: 18/146,139

(22) Filed: Dec. 23, 2022

(65) Prior Publication Data
US 2024/0206906 A1 Jun. 27, 2024

(51) Int. Cl.
 *A61B 17/34* (2006.01)
 *A61B 34/10* (2016.01)
 *A61B 34/20* (2016.01)

(52) U.S. Cl.
CPC .......... *A61B 17/3403* (2013.01); *A61B 34/10* (2016.02); *A61B 34/20* (2016.02); *A61B 2034/102* (2016.02); *A61B 2034/104* (2016.02); *A61B 2034/105* (2016.02);
(Continued)

(58) Field of Classification Search
CPC ..... A61B 17/3403; A61B 34/10; A61B 34/20; A61B 2034/102; A61B 2034/104; A61B 2034/105; A61B 2034/2051; A61B 2034/2063; A61B 2034/2065; A61B 2034/107; A61B 18/1492; A61B 2017/00247; A61B 2018/00577; A61B 2034/2053; A61B 34/25; A61B 17/3478
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,462,545 A | 10/1995 | Wang et al. |

(Continued)

FOREIGN PATENT DOCUMENTS

| | | |
|---|---|---|
| CN | 114748136 A | 7/2022 |
| EP | 1 034 738 A1 | 9/2000 |

(Continued)

OTHER PUBLICATIONS

Extended European Search Report and Opinion dated May 28, 2024, from corresponding European Application No. 23219679.0.

*Primary Examiner* — Alexei Bykhovski (57) ABSTRACT

A tool to determine a pre-puncture needle shape to provide a desired approach to a target location based on measured patient anatomy is disclosed herein. Anatomical relationship between an outlet of an access vessel and a desired puncture sight on the interatrial septum is used to determine the pre-puncture needle shape. The tool may be used to provide a recommended preferred needle shape from a collection of predetermined needle shapes (e.g. commercially available needle shapes) and/or recommend a bent shape to which a physician may modify a predetermined needle shape to fit. Additionally, or alternatively, the tool may be used to provide a recommended preferred needle shape to manufacturers to create a bespoke needle shape for a given patient and/or a recommended preferred needle shape for patient cohort having similar anatomy within the cohort.

15 Claims, 8 Drawing Sheets

(52) U.S. Cl.
CPC ............... *A61B 2034/2051* (2016.02); *A61B 2034/2063* (2016.02); *A61B 2034/2065* (2016.02)

(56) References Cited

U.S. PATENT DOCUMENTS

| | | | |
|---|---|---|---|
| 5,558,091 | A | 9/1996 | Acker et al. |
| 5,807,350 | A | 9/1998 | Diaz |
| 6,172,499 | B1 | 1/2001 | Ashe |
| 6,239,724 | B1 | 5/2001 | Boron et al. |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 6,788,967 | B2 | 9/2004 | Ben-Haim et al. |
| 6,892,091 | B1 | 5/2005 | Ben-Haim et al. |
| 7,536,218 | B2 | 5/2009 | Govari et al. |
| 7,756,576 | B2 | 7/2010 | Levin |
| 7,848,787 | B2 | 12/2010 | Osadchy |
| 7,869,865 | B2 | 1/2011 | Govari et al. |
| 8,235,986 | B2 | 8/2012 | Kulesa et al. |
| 8,456,182 | B2 | 6/2013 | Bar-Tel et al. |
| 9,326,813 | B2 | 5/2016 | Pike, Jr. et al. |
| 10,065,032 | B2 | 9/2018 | Ollivier |
| 10,194,937 | B2 | 2/2019 | Schultz |
| 10,413,707 | B2 | 9/2019 | Douglas |
| 2003/0018246 | A1 | 1/2003 | Govari et al. |
| 2004/0082860 | A1 | 4/2004 | Haissaguerre |
| 2004/0220471 | A1 | 11/2004 | Schwartz |
| 2005/0055089 | A1 | 5/2005 | Macoviak et al. |
| 2012/0232546 | A1 | 9/2012 | Mirza et al. |
| 2015/0182255 | A1* | 7/2015 | Shivkumar ........ A61B 17/3415 606/108 |
| 2017/0014113 | A1* | 1/2017 | Ma ..................... A61B 17/0057 |
| 2018/0154114 | A1 | 6/2018 | Tang et al. |
| 2019/0000551 | A1 | 1/2019 | Sone et al. |
| 2019/0083187 | A1* | 3/2019 | Danitz ................... A61B 18/14 |
| 2020/0261158 | A1 | 8/2020 | Ward et al. |
| 2021/0334999 | A1* | 10/2021 | Lee ....................... A61B 6/5217 |
| 2021/0401483 | A1 | 12/2021 | Highsmith |
| 2022/0133261 | A1 | 5/2022 | Urman et al. |

FOREIGN PATENT DOCUMENTS

| | | |
|---|---|---|
| EP | 1 325 708 A2 | 7/2003 |
| EP | 1 472 976 A1 | 11/2004 |
| WO | WO 96/05768 A1 | 2/1996 |
| WO | WO 99/39624 A1 | 8/1999 |
| WO | WO 01/80922 A2 | 11/2001 |
| WO | WO 02/071955 A2 | 9/2002 |
| WO | WO 2014162470 * | 10/2014 |

* cited by examiner

RECOMMENDING TRANSSEPTAL NEEDLE CURVATURE BASED ON ANATOMY

FIELD

The present invention relates generally to catheter-based treatments, and specifically to trans-septal perforation in the heart.

BACKGROUND

The transseptal puncture (TP) technique was introduced into clinical practice during the late 1950s as a diagnostic tool to select patients for cardiac valve surgery. Usefulness of TP has evolved since to include left heart electrophysiology ablations, percutaneous mitral valve repair/implantation, patent foramen ovale closure, left atrial appendage occlusion, paraprosthetic valve leak repair, and left ventricular assist device positioning.

Methods for performing TP typically include a preprocedural assessment which involves imaging of the interatrial septum (IS). The fossa ovalis is within a portion of the IS which is an area that may be crossed without going into extracardiac space and is a desired puncture location due to its composition of thin fibrous tissue. Anatomy varies between patients, and equipment for performing TP may be selected based on the specific anatomy of the patient. Equipment typically includes a needle, a dilator, and a sheath. A "needle" as used herein means any device configured to access targeted tissue via a blood vessel and to puncture the targeted tissue, whether by mechanical force or by the application of energy (e.g., radiofrequency (RF) or pulsed high-voltage energy as employed in pulsed-field ablation). A variety of needles and sheaths with a pre-curved distal end are available to choose from, and a needle and/or sheath with a desired curvature may be selected based on anatomy of the patient. The sheath is guided to enter the right atrium through an access vessel, such as the superior vena cava (SVC) or the inferior vena cava (IVC). The dilator and needle are delivered through the sheath to the IS. The needle is used to puncture the IS, and the dilator and sheath cross the IS after the needle. The needle is then removed and catheters are delivered through the sheath across the IS. The curvature of the needle may affect the approach of the needle to the IS. In some treatments, a physician may bend the needle by hand, prior to delivering the needle through the dilator and sheath, to attempt to achieve a desired angle of approach to the IS. This bending is done by hand and relies on either pre-imaging guidance or electromagnetic mapping geometry, which is at least a somewhat blind and subjective process.

SUMMARY

Examples illustrated herein generally provide a tool to determine a pre-puncture needle shape to provide a desired approach to a target location based on measured patient anatomy. Examples illustrated herein specifically rely on anatomical relationship between an outlet of an access vessel and a desired puncture sight on the IS to determine the pre-puncture needle shape. The tool may be used to provide a recommended preferred needle shape from a collection of predetermined needle shapes (e.g. commercially available needle shapes) and/or recommend a bent shape to which a physician may modify a predetermined needle shape to fit. Additionally, or alternatively, the tool may be used to provide a recommended preferred needle shape to manufacturers to create a bespoke needle shape for a given patient and/or a recommended preferred needle shape for patient cohort having similar anatomy within the cohort.

An example system may include a processor and non-transitory computer-readable medium. The non-transitory computer-readable medium may include instructions thereon, that when executed by the processor, cause the system to determine a curvature of a transseptal needle based at least in part on a spatial relationship between an access vessel and a target puncture location.

The access vessel may include the inferior vena cava.

The access vessel may include the superior vena cava.

The instructions may further be configured to cause the system to determine the spatial relationship between the access vessel and the target puncture location.

The instructions may further be configured to cause the system to generate an anatomical map. The anatomical map may include an access vessel approximate a right atrium and at least a portion of an interatrial septum of the right atrium. The instructions may further be configured to cause the system to identify, based on the anatomical map, a location of the access vessel approximate the right atrium and the target puncture location. The instructions may further be configured to cause the system to determine the spatial relationship between the access vessel and the target puncture location. The spatial relationship may be confirmed with intracardiac fluoroscopy and/or ultrasound data.

The instructions may further be configured to cause the system to generate the anatomical map based at least in part on electromagnetic mapping.

The system may further include a display. The instructions may further be configured to cause the system to display a recommended curvature of the transseptal needle on the display.

The instructions may further be configured to cause the system to receive an indication of needle selection indicating one predetermined needle shape of a plurality of predetermined needle shapes. The instructions may further be configured to cause the system to determine the curvature based at least in part on the indication of needle selection.

The instructions may further be configured to cause the system to determine a deployed position of the predetermined needle shape such that a proximal point of the predetermined needle shape is positioned at the access vessel and a distal point of the predetermined needle shape is positioned at an interatrial septum. The instructions may further be configured to cause the system to determine the curvature using a rotational matrix to move the distal point to the target puncture location while holding the proximal point fixed.

The system may further include a needle identification module configured to receive the indication of needle selection.

The needle identification module may be configured to receive a needle identifier from an electrically erasable programmable read-only memory (EEPROM) of a needle in communication with the system and may be configured to determine the indication of needle selection based at least in part on the needle identifier.

The instructions may further be configured to cause the system to select, based at least in part on the curvature of the transseptal needle, a preferred needle shape from a plurality of predetermined needle shapes.

The instructions may further be configured to cause the system to recommend, to a user of the system, the preferred needle shape.

The instructions may further be configured to cause the system to recommend a transseptal needle design based at least in part on the curvature.

An example method for transseptal puncture may include the following steps executed in a variety of orders and with interleaving steps as understood by a person skilled in the art. The method may include displaying, on a display, an anatomical map of a patient. The method may include receiving, from a user interface, a first location, on the anatomical map, at an outlet of an inferior vena cava. The method may include receiving, from the user interface, a second location, on the cardiac map, at a desired puncture site on a fossa ovalis. The method may include extrapolating a curve between the first location and the second location. The method may include providing, on the display, a needle shape template based at least in part on the extrapolated curve.

The method may include determining the needle shape template based at least in part on a predetermined needle shape.

The method may include determining a deployed position of the predetermined needle shape such that a proximal point of the predetermined needle shape is positioned at the first location and a distal point of the predetermined needle shape is positioned at the interatrial septum. The method may include determining a curvature of the needle shape template using a rotational matrix to move the distal point to the desired puncture site while holding the proximal point fixed.

The method may include recommending a predetermine needle shape.

An example method for facilitating transseptal puncture may include the following steps executed in a variety of orders and with interleaving steps as understood by a person skilled in the art. The method may include identifying, on an anatomical map, a first location at an outlet of an access vessel. The method may include identifying, on the anatomical map, a second location at a desired puncture site on the fossa ovalis. The method may include displaying a template curvature of a transseptal needle, the template curvature being based at least in part on a spatial relationship between the first location and the second location.

Another example method may include determining a patient-specific transseptal needle curvature for the patient based at least in part on a spatial relationship between an outlet of an access vessel of a heart of the patient and a desired puncture site on the fossa ovalis of the patient.

Another example method may include determining a transseptal needle curvature based at least in part on a plurality of spatial relationships each between a respective outlet of an access vessel and the respective fossa ovalis.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

In addition, as used herein, the terms "patient," "host," "user," and "subject" refer to any human or animal subject and are not intended to limit the systems or methods to human use, although use of the subject invention in a human patient represents a preferred embodiment. As well, the term "proximal" indicates a location closer to the operator whereas "distal" indicates a location further away to the operator or physician.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the pertinent art in view of the teachings herein. Such modifications and variations are intended to be included within the scope of the claims.

Figure 1:
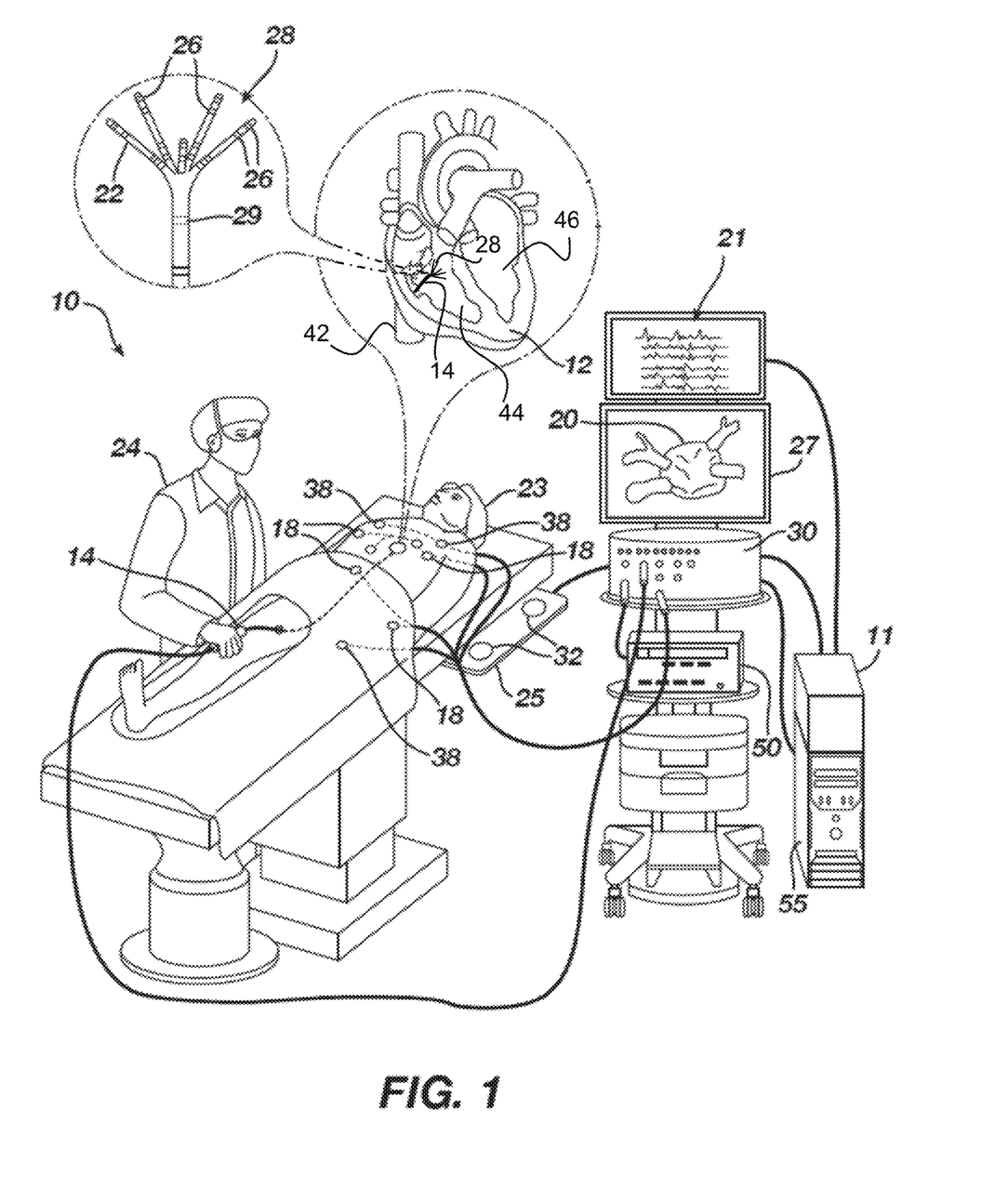
FIG. 1 is an illustration of an example catheter-based electrophysiology mapping and ablation system according to aspects of the present invention.

FIG. 1 is an illustration showing an example catheter-based electrophysiology mapping and ablation system 10. The system 10 includes multiple catheters, which are percutaneously inserted by a physician 24 through the patient's vascular system into a chamber or vascular structure of a heart 12. Typically, a delivery sheath catheter is inserted into the left atrium 46 or right atrium 44 near a desired location in the heart 12. Thereafter, a plurality of catheters may be inserted into the delivery sheath catheter so as to arrive at the desired location. The plurality of catheters may include catheters dedicated for sensing Intracardiac Electrogram (IEGM) signals, catheters dedicated for ablating and/or catheters which may perform both sensing and ablating. An example catheter 14 that is configured for sensing IEGM is illustrated herein. The physician 24 brings a distal tip 28 of the catheter 14 into contact with the heart wall for sensing a target site in the heart 12. For ablation, the physician 24 would similarly bring a distal end of an ablation catheter to a target site for ablating.

The illustrated catheter 14 is an exemplary catheter that includes one and preferably multiple electrodes 26 optionally distributed over a plurality of spines 22 at distal tip 28 and configured to sense the IEGM signals. Catheter 14 may additionally include a position sensor 29 embedded in or near distal tip 28 for tracking position and orientation of distal tip 28. Optionally and preferably, position sensor 29 is a magnetic based position sensor including three magnetic coils for sensing three-dimensional (3D) position and orientation.

A magnetic based position sensor 29 may be operated together with a location pad 25 including a plurality of magnetic coils 32 configured to generate magnetic fields in a predefined working volume. Real time position of a distal tip 28 of the catheter 14 may be tracked based on magnetic fields generated with a location pad 25 and sensed by a magnetic based position sensor 29. Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091 incorporated by reference herein.

The system 10 may include one or more electrode patches 38 positioned for skin contact on the patient 23 to establish location reference for location pad 25 as well as impedance-based tracking of electrodes 26. For impedance-based tracking, electrical current is directed toward electrodes 26 and sensed at electrode skin patches 38 so that the location of each electrode may be triangulated via the electrode patches 38. Details of the impedance-based location tracking technology are described in U.S. Pat. Nos. 7,536,218; 7,756,576; 7,848,787; 7,869,865; and 8,456,182 incorporated by reference herein.

A recorder 11 displays electrograms 21 captured with body surface ECG electrodes 18 and intracardiac electrograms (IEGM) captured with electrodes 26 of the catheter 14. The recorder 11 may include pacing capability for pacing the heart rhythm and/or may be electrically connected to a standalone pacer.

The system 10 may include an ablation energy generator 50 that is adapted to conduct ablative energy to one or more of electrodes at a distal tip of a catheter configured for ablating. Energy produced by the ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

A patient interface unit (PIU) 30 is an interface configured to establish electrical communication between catheters, electrophysiological equipment, power supply and a workstation 55 for controlling operation of system 10. Electrophysiological equipment of the system 10 may include for example, multiple catheters, a location pad 25, body surface ECG electrodes 18, electrode patches 38, an ablation energy generator 50, and a recorder 11. Optionally and preferably, the PIU 30 includes processing capability for implementing real-time computations of location of the catheters and for performing ECG calculations.

The workstation 55 includes memory, processor unit with memory or storage with appropriate operating software loaded therein, and user interface capability. The workstation 55 may be configured to provide multiple functions, optionally including (1) modeling the endocardial anatomy in three-dimensions (3D); (2) rendering the model or an anatomical map 20 for display on a display device 27; (3) displaying on the display device 27 activation sequences (or other data) compiled from recorded electrograms 21 in representative visual indicia or imagery superimposed on the rendered anatomical map 20; (4) displaying real-time location and orientation of multiple catheters within the heart chamber; and (5) displaying on the display device 27 sites of interest such as places where ablation energy has been applied. One commercial product embodying elements of the system 10 is available as the CARTO® 3 System, available from Biosense Webster, Inc., 31A Technology Drive, Irvine, CA 92618.

The display device 27 may include a touchscreen to provide a user interface to the workstation 55. The system 10 may additionally include other user interface devices to the workstation 55 such as a keyboard, mouse, joystick, handheld control, button interface, etc. as understood by a person skilled in the art.

The workstation 55 may further be configured to determine a pre-puncture needle shape of a transseptal needle to provide a desired approach to a target location based on measured patient anatomy.

Figure 2:
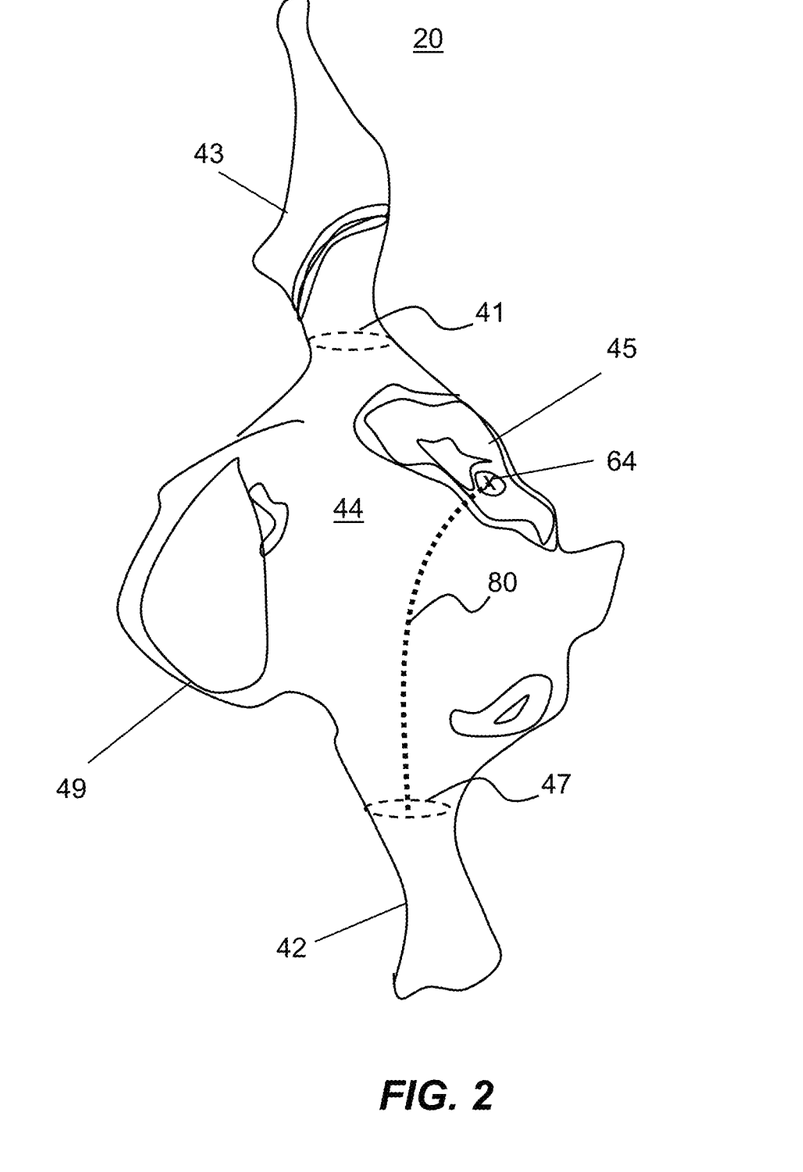
FIG. 2 is an illustration of an example anatomical map of a portion of a heart according at aspects of the present invention.

FIG. 2 is an illustration of an example anatomical map 20 of a portion of the heart 12 illustrated in FIG. 1. The distal tip 28 of the catheter 14 of FIG. 1 may be moved across tissue in the right atrium 44, inferior vena cava 42, and superior vena cava 43, and signals from the electrodes 26 and/or sensor 29 of the catheter 14 may be used by the workstation 55 to generate the anatomical map 20 illustrated in FIG. 2. The system 10 may additionally, or alternatively use static fluoroscopy images to merge with real-time cardiac maps. The system 10 may additionally, or alternatively use 3D ultrasound technology to enhance the anatomical map 20. The map 20 shows the relationship between the access vessels 42, 43 and the right atrium 44 at shows the fossa ovalis 45 which is on the interatrial septum of the right atrium 44. The map 20 illustrates the tricuspid annulus 49 for reference. The anatomical map 20 illustrated in FIG. 2 may be displayed on the display 27 illustrated in FIG. 1.

In current treatment transseptal puncture procedures, electrophysiologists select curvature of a transseptal needle based on either pre-imaging guidance or an electroanatomical map, an anatomical model, or imaging data (e.g., 2D, 3D, or 4D ultrasound data), all of which are referred to interchangeably herein as a "map" or "imaging." An exemplary electroanatomical map 20 is illustrated in FIG. 2. In some of these procedures, the electrophysiologist also shapes the transseptal needle, pre-puncture, without much additional information beyond the pre-imaging guidance or an electroanatomical map. The physician hand shapes the transseptal needle to fit the atrium, in an attempt to target the best position on the fossa ovalis for transseptal puncture.

An aspect of the current invention is to provide a tool to determine a preferred pre-puncture needle shape of a transseptal needle to provide a desired approach to a target location based on measured patient anatomy. Using the system 10 illustrated in FIG. 1, the physician 24 may use the user interface to the workstation 55 to mark, or otherwise indicate, (1) an outlet 47 of the inferior vena cava 42 into the right atrium 44, and (2) a target puncture location 64 on the fossa ovalis 45 on the map 20. The workstation 55 may be configured to extrapolate a curve 80 between the outlet 47 of the inferior vena cava and the target puncture location 64.

The extrapolated curve 80 may be used to determine a curvature of a transseptal needle.

The outlet 47 of the inferior vena cava 42 may be marked with an oval as illustrated to provide for greater accuracy or with a point to simplify marking by the physician 24 and calculation by the workstation 55. The outlet of the target puncture location 64 is preferably marked with a point as illustrated for greater accuracy and to simplify marking and calculation, but may be marked with an oval or other shape or visual indication to provide for more options in predetermined needle selection (FIGS. 3 and 4) and/or simplify the recommended curvature of a modified needle shape (FIGS. 5A and 5B).

While examples presented herein focus on modifying the most common transseptal needle puncture practice which involves inserting the needle through the inferior vena cava 42, through the right atrium 44, and across the fossa ovalis 45, the tool may be modified for other procedures. For instance, the access vessel may be the superior vena cava 43, in which case the workstation 55 may be configured to mark, or otherwise indicate an outlet 41 of the superior vena cava 43 instead of the outlet 47 of the inferior vena cava 42. The workstation 55 may be configured to determine the spatial relationship between the access vessel and the target puncture location.

The tool may be modified for instances in which a desired pre-shaped curvature is needed to position a distal end of an intralumenal medical device against tissue, and the shaft of the medical device may be approximated as being fixed within a confined space such as an outlet of a blood vessel or other bodily lumen into a larger chamber.

As an alternative to displaying the map 20 and allowing the physician 24 to mark the outlet of the access vessel (e.g. outlet 47 of inferior vena cava 42) and the target puncture location 64, the workstation 55 may be configured to automatically determine the positions of these features based on IEGM data collected from the electrodes 26 (FIG. 1), and/or based on general anatomical shape of the heart 12 determined by other means such as ultrasound, or detection of force against tissue. When the workstation 55 determines the positions of the outlet of the access vessel and the target puncture location 64, the workstation 55 need not provide the map 20 on the display 27 for the purposes of determining needle curvature, but may provide the map 20 on the display 27 for other needs during a procedure.

The tool may also be used to design a new transeptal needle having a curvature that approximates the extrapolated curve 80. For instance, a transseptal needle may be made bespoke for a patient ahead of a procedure, and/or a transseptal needle may be designed based on extrapolated curves 80 from multiple patients with similar anatomy and averaged to meet the needs of multiple patients. The workstation 55 may be configured to determine a patient-specific transseptal needle curvature for the patient based at least in part on a spatial relationship between an outlet of an access vessel of a heart of the patient and a desired puncture site on the fossa ovalis of the patient. Additionally, or alternatively, the workstation 55 may be configured to determine a transseptal needle curvature based at least in part on a plurality of spatial relationships each between a respective outlet of an access vessel and the respective fossa ovalis.

Figure 3:
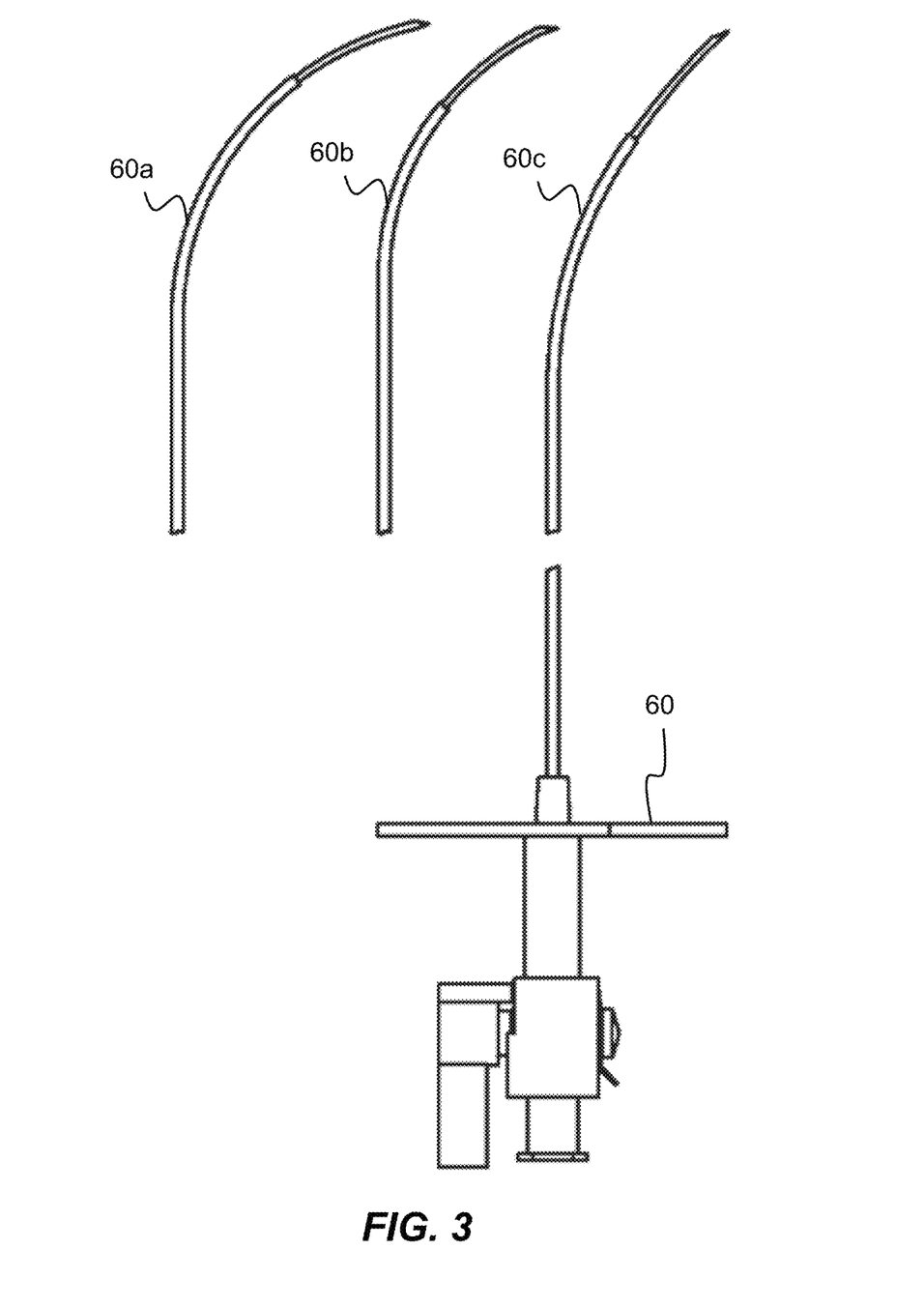
FIG. 3 is an illustration of a transseptal needle and predetermined needle shapes.

FIG. 3 is an illustration of a transseptal needle 60 and predetermined needle shapes 60a. 60b, 60c. As illustrated, the predetermined needle shape 60a on the left has the smallest radius of curvature, tightest bend; the predetermined needle shape 60b in the middle has a larger radius of curvature, less of a bend compared to the left shape 60a; and the predetermined needle shape 60c on the right has the largest radius of curvature, least bend compared to the left shape 60a and middle shape 60b.

The illustrated predetermined needle shapes may be as-manufactured, and the workstation 55 may be configured with a catalogue of predetermined needle shapes that the physician 24 may have access to. The workstation 55 may be configured to select a preferred needle shape from the predetermined needle shapes in the catalogue based on the extrapolated curve between the outlet 47 of the inferior vena cava and the marked target puncture location 64. The preferred needle shape may have a distal tip that is closely aligned with the desired puncture site 64 when the shaft of the needle is positioned through the outlet 47 of the inferior vena cava 42. To achieve this, the preferred needle shape may have a similar radius of curvature, or similar overall bent shape compared to the extrapolated curve.

The workstation 55 (FIG. 1) may be configured to recommend the preferred needle shape to the physician 24 by displaying the product name and catalogue number on the display 27 or otherwise providing an indication of the preferred needle shape as understood by a person skilled in the art.

Figure 4:
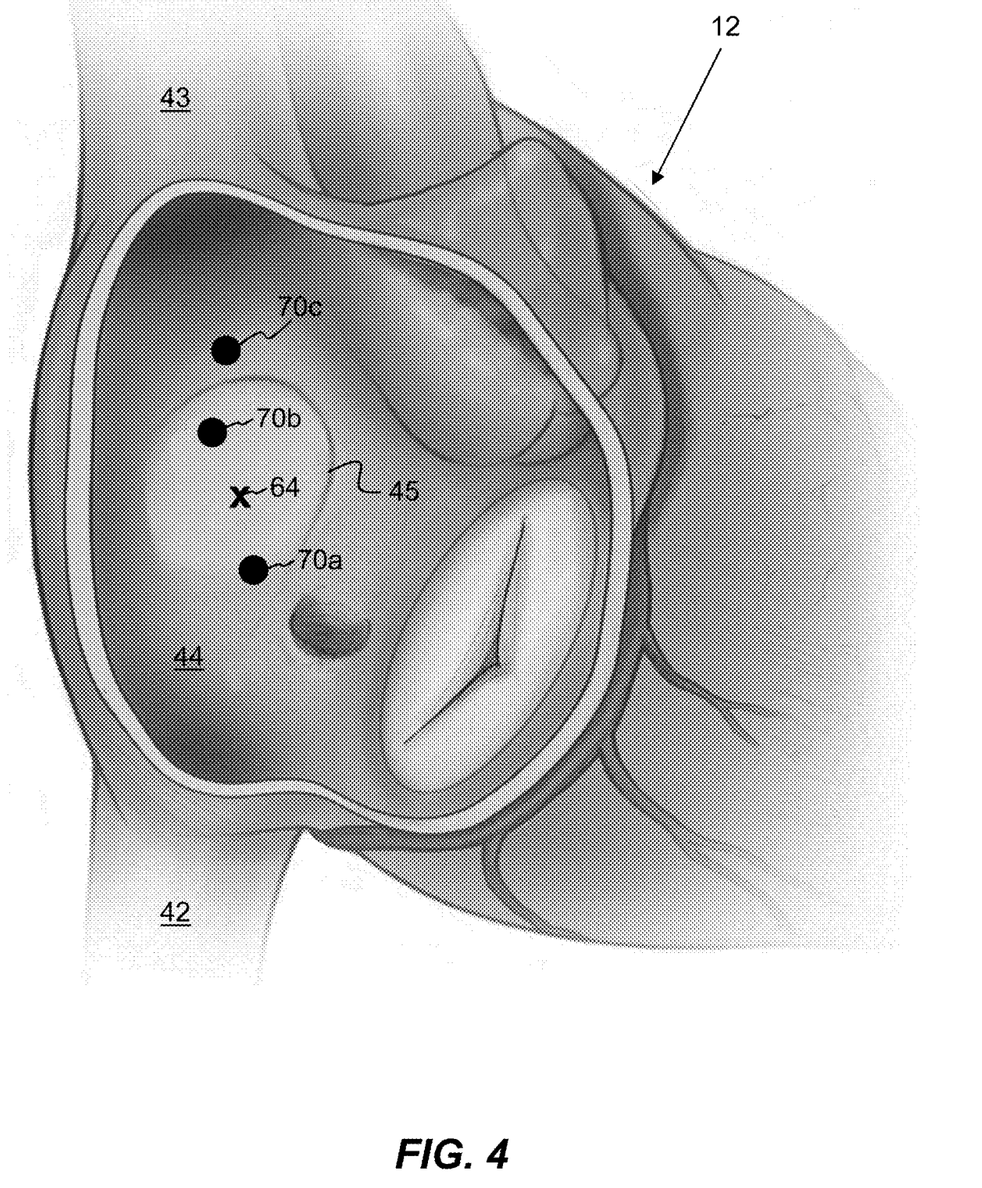
FIG. 4 is a diagram of a heart illustrating possible puncture locations using the predetermined needle shapes of FIG. 3 and a target puncture location according at aspects of the present invention.
Figure 5A:
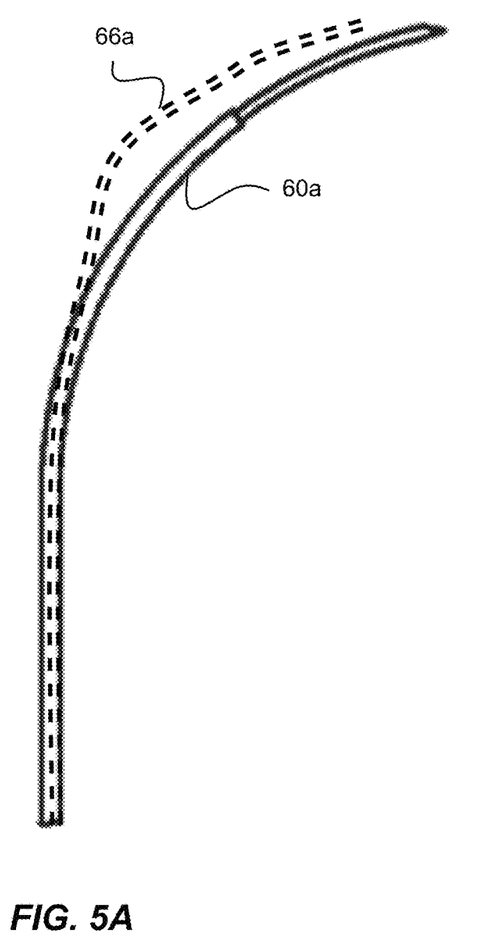
FIG. 5A and FIG. 5B are illustrations of a recommended curvature of a needle shape in comparison to two different predetermined needle shapes according at aspects of the present invention.
Figure 5B:
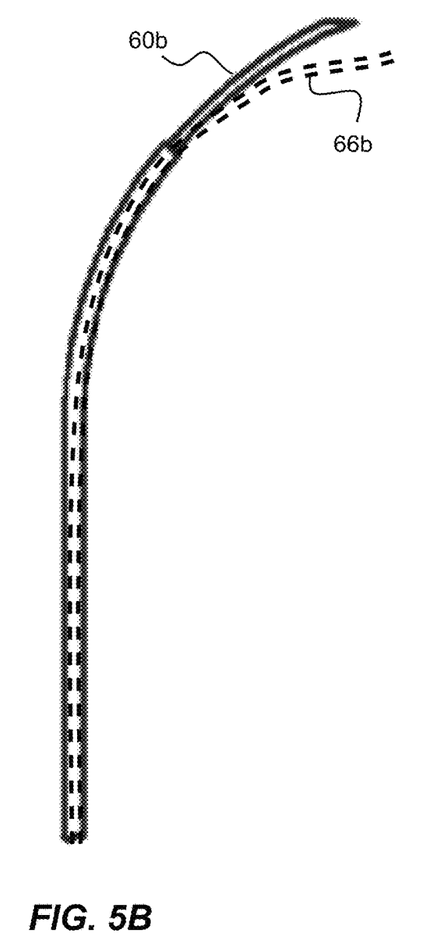

FIG. 4 is a diagram of the heart 12 illustrating possible puncture locations 70a, 70b, 70c using the predetermined needle shapes 60a, 60b, 60c of FIG. 3 and the target puncture location 64. The tight curvature of the left predetermined needle shape 60a (FIG. 3) results in a possible puncture location 70a inferior of the target puncture location 64 and on an edge of the fossa ovalis 45. The middle predetermined needle shape 60b (FIG. 3) results in a possible puncture location 70b on the fossa ovalis 45 and superior of the target puncture site location 64. The large radius of curvature of the right predetermined needle shape 60c (FIG. 3) results in a possible puncture location 70c superior of the fossa ovalis 45.

The workstation 55 (FIG. 1) may be configured to predict the possible puncture locations 70a, 70b, 70c of the predetermined needle shapes 60a, 60b, 60c based on the location of the outlet 47 of the inferior vena cava 42 and the target puncture location 64 (FIG. 2). When each needle 60 is in a deployed position, a proximal point of the predetermined needle shape is positioned at the access vessel and a distal point of the predetermined needle shape is positioned at the interatrial septum.

The workstation 55 (FIG. 1) may be configured to select the preferred needle shape based on the location of the possible puncture locations 70a, 70b, 70c. The workstation 55 may be configured to select the preferred needle shape based on distance between the possible puncture locations 70a, 70b, 70c. The workstation 55 may also be configured to take into account the location of the possible puncture locations 70a, 70b, 70c in relation to the fossa ovalis 45, giving a priority to a predetermined needle shape that is on the fossa ovalis 45.

In the illustrated example, the workstation 55 (FIG. 1) may be configured to recommend the middle predetermined needle shape 60b because this needle shape is determined to have a possible puncture location 70b that is approximately as close, or closer, to the target puncture location 64 compared to the possible puncture locations 70a, 70c of the left predetermined needle shape 60a and the right predetermined needle shape 60c (FIG. 3), and the possible puncture location 70b of the middle predetermined needle shape 60b is more centrally located on the fossa ovalis 45 compared to the possible puncture location 70a of the left predetermined needle shape 60a.

FIG. 5A and FIG. 5B are illustrations of a recommended curvature 66a, 66b of a needle shape in comparison to two different predetermined needle shapes 60a, 60b. In some implementations of the tool, the workstation 55 may provide a template on the screen 27 (FIG. 1) for an optimal needle shape. The recommended curvature 66a, 66b may be displayed, to scale, on the display 27, so that the physician 24 may hold the needle that will be used for the procedure, to the display, to compare modified curvature of the needle to the recommended curvature 66a, 66b. The workstation (FIG. 1) may be configured to determine a deployed position of the predetermined needle shape such that a proximal point of the predetermined needle shape is positioned at the access vessel (e.g. at outlet 47 of the inferior vena cava 42 in FIG. 2) and a distal point of the predetermined needle shape is positioned at an interatrial septum (e.g. at target puncture location 64 in FIG. 2).

The workstation 55 may be configured to determine the curvature of the modified needle shape using a rotational matrix to move the distal point to the target puncture location 64 while holding the proximal point fixed. For instance, the workstation 55 may have information regarding the predetermined needle shape 60a, 60b of the needled used by the physician 24, and the puncture location 64 (FIG. 4) may be located by a device that includes a location sensor. The workstation 55 may have information indicating the entry port 47, e.g. the location of the IVC 42. This is the starting position of calculation. The shape of the needle 60 may be modeled by a few rigid sections, minimum two, maximum six, preferably three or four rigid sections. The rigid sections are connected by joints. Each section is defined relative to the last section (adjacent section in the proximal direction) it is connected to, except for the first, proximal most section, which is defined relative to the entry point 47. Each section is determined by a set of rotation matrices, one for each section, except for the first section which is defined by the entry point 47. The target of the last section is the target puncture location 64 (FIG. 4).

For instance, the physician 24 (FIG. 1) may desire to shape a predetermined needle shape 60a, 60b to modify the possible puncture location 70a. 70b of that needle to approach the target puncture location 64 (FIG. 4). This may be done after the workstation 55 provides the recommendation for preferred predetermined needle shape as discussed in greater detail in relation to FIGS. 3 and 4. The physician 24 may select the predetermined needle shape and choose to modify it further. Alternatively, the physician 24 may use some other predetermined needle shape and may choose to modify the other needle shape. For instance, the physician 24 may not have access to the recommended needle, and may choose a different needle based on what is available. In this case, using the illustrated example, the workstation 55 may be configured to provide additional options for predetermined needle shape, and may recommend the left predetermined needle shape 60a (FIG. 5A and FIG. 3) because the possible puncture location 70a is preferred over the remaining option. In the illustrated example, if the needle used treatment has a curvature 60a as illustrated in FIG. 5A, the recommended curvature 66a may be determined for that needle shape and displayed against that needle shape on the display 27 for comparison. Likewise, if the needle used has a curvature 60b as illustrated in Figure B, the recommended curvature 66b and predetermined needle curvature 60b illustrated in FIG. 5B may be displayed on the display 27.

In an alternative example, the workstation 55 need not be configured to provide a preferred predetermined needle shape, and the workstation 55 may be configured to determine the recommended curvature 66a, 66b generically for a wide range of predetermined needle shapes that the physician 24 is likely to choose from. The recommended curvature 66a, 66b may be displayed without a predetermined needle shape for comparison.

In another alternative example, the workstation 55 need not be configured to provide a preferred predetermined needle shape, and the workstation 55 may be configured to determine the recommended curvature 66a, 66b based on a predetermined needle shape selection input to the workstation 55. For instance, the workstation 55 may be configured to provide a list of possible needles to the physician 24, the physician 24 may select a needle from the list, and the workstation 55 may determine the recommended curvature 66a, 66b based on the predetermined needle shape 60a, 60b of the selected needle. Additionally, or alternatively, the workstation 55 may be configured to automatically identify the selected needle from the catalogue of needles stored in the workstation 55, for instance by using a quick read (QR) code, an electrically erasable programmable read-only memory (EEPROM), a radio frequency identification (RFID), etc. as understood by a person skilled in the art. For instance, the workstation 55 may include a needle identification module configured to receive the indication of needle selection. The needle identification module may be configured to receive a needle identifier from an electrically erasable programmable read-only memory (EEPROM) of a needle in communication with the system and may be configured to determine the indication of needle selection based at least in part on the needle identifier.

Given that the workstation 55 is provided information on the selected needle, the workstation 55 may be pre-configured with information on the shape and length of the selected needle. With the dimensions of the needle, the target puncture location 64, and the location of the outlet 47 of the inferior vena cava 42 (FIG. 2), a point of the needle shaft that passes through the inferior vena cava 42 may be fixed in place, and an angle of change to fit the selected needle curve may be determined so that the distal tip of the needle is at or near the target puncture location 64. In one example, the new distal end of the needle may be calculated by implementing a rotation matrix to shift the most distal point of the needle to the desired position at the target puncture location 64 and translating other points proximally along the needle to the shaft fixed to the outlet 47 of the inferior vena cava 42. The calculated curvature may be displayed as the recommended curvature 66a, 66b.

In a situation in which the curvature 80 (FIG. 2) is determined automatically by the workstation 55 without input from the physician 24, the anatomical map 20 (FIG. 2) need not be displayed on the display for the purposes of needle selection or shape determination, and it may be sufficient to display the recommended curvature 66a, 66b for the physician 24 to be able to shape the selected needle.

Figure 6:
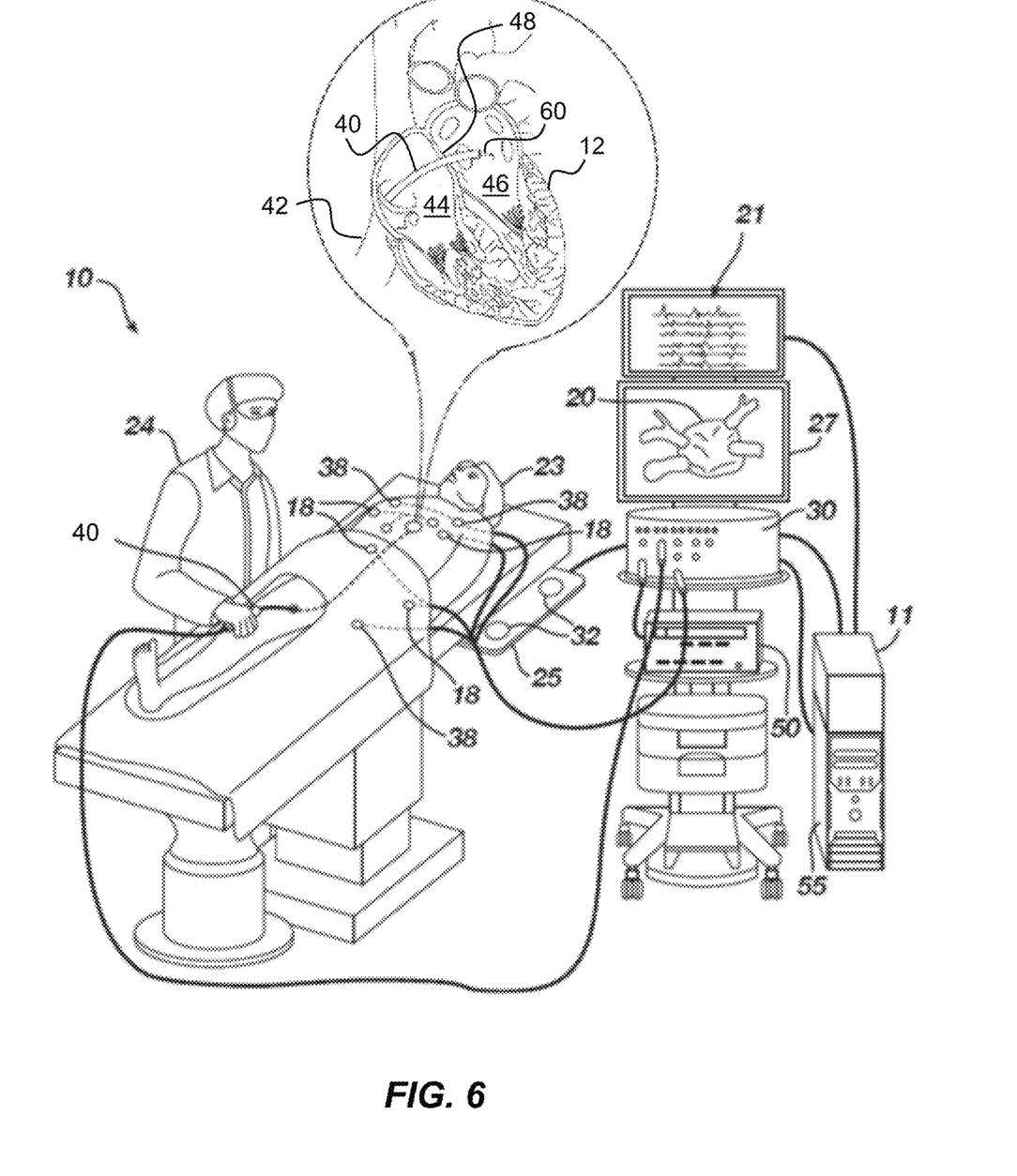
FIG. 6 is an illustration of a transseptal puncture procedure according at aspects of the present invention.

FIG. 6 is an illustration of a transseptal puncture procedure using the system 10 illustrated in FIG. 1. A sheath 40 is delivered through the femoral artery, the inferior vena cava 42, and into the right atrium 44. The sheath 40 is positioned through an opening in the interatrial septum 48 made by the needle 60. The needle 60 may be retracted while the distal end of the sheath 40 is in the left atrium 46 to allow for catheters to be delivered to the left atrium 46.

Figure 7:
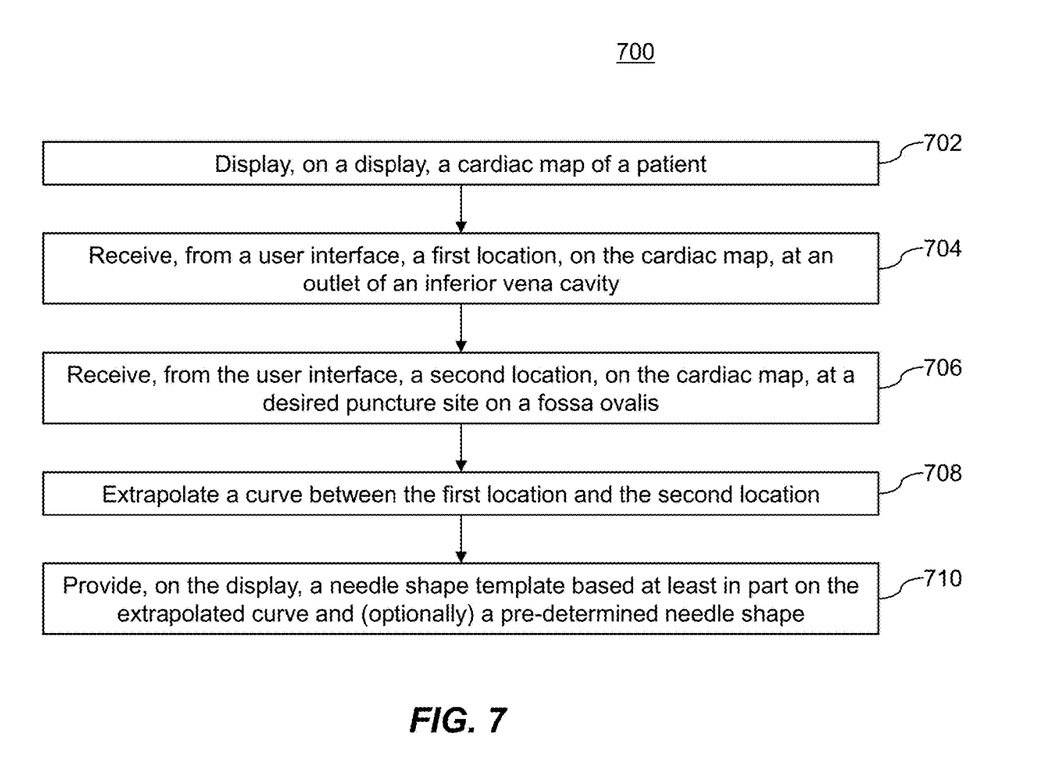
FIG. 7 is a flow diagram including method steps for an example method for transseptal puncture according at aspects of the present invention.

FIG. 7 is a flow diagram including method steps for an example method 700 for transseptal puncture. The method 700 may be performed by the system 10 illustrated in FIGS. 1 and 6, variations thereof as disclosed herein, and alternatives thereto as understood by a person skilled in the art. In particular, instructions to perform the method 700 may be stored in memory of the workstation 55 and may be executed by the processor(s) of the workstation 55 to cause the system 10 to execute steps of the method 700.

At block 702, a cardiac map of a patient may be displayed on a display. The cardiac map may be configured similarly to the cardiac map 20 illustrated in FIGS. 1 and 2, variations thereof, and alternatives thereto as understood by a person skilled in the art. The display may be configured similar to display 27 illustrated in FIG. 1, variations thereof, and alternatives thereto as understood by a person skilled in the art.

At block 704, a first location, on the cardiac map, at an outlet of the inferior vena cavity, may be received from a user interface.

At block 706, a second location, on the cardiac map, at a desired puncture site on a fossa ovalis, may be received from the user interface.

At block 708, a curve between the first location and the second location may be extrapolated.

At block 710, a needle shape template may be provided on the display. The needle shape template may be based at least in part on the extrapolated curve and (optionally) a predetermined needle shape.

When the needle shape template is based on the predetermined needle shape, a deployed position of the predetermined needle shape may be determined such that a proximal point of the predetermined needle shape is positioned at the first location and a distal point of the predetermined needle shape is positioned at the interatrial septum. A curvature of the needle shape template may be determined using a rotational matrix to move the distal point to the desired puncture site while holding the proximal point fixed. The method 700 may further include recommending the predetermined needle shape.

Figure 8:
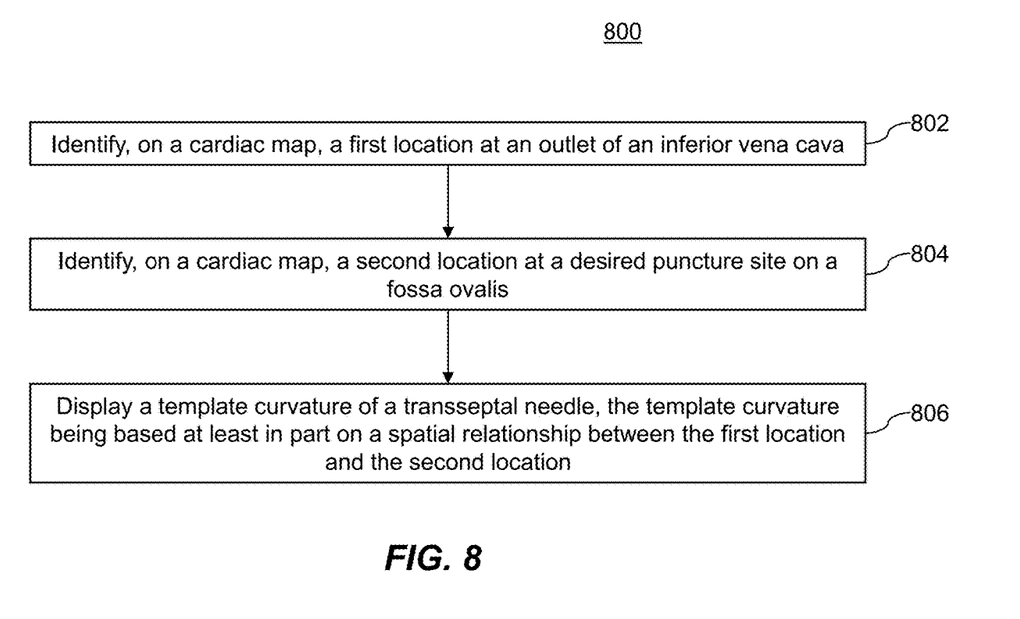
FIG. 8 is a flow diagram including method steps for an example method for facilitating transseptal puncture according at aspects of the present invention.

FIG. 8 is a flow diagram including method steps for an example method 800 for facilitating transseptal puncture. The method 800 may be performed by the system 10 illustrated in FIGS. 1 and 6, variations thereof as disclosed herein, and alternatives thereto as understood by a person skilled in the art. In particular, instructions to perform the method 800 may be stored in memory of the workstation 55 and may be executed by the processor(s) of the workstation 55 to cause the system 10 to execute steps of the method 800.

At step 802, a first location, at an outlet of an inferior vena cava, may be identified on a cardiac map. The cardiac map may be configured similarly to the cardiac map 20 illustrated in FIGS. 1 and 2, variations thereof, and alternatives thereto as understood by a person skilled in the art. The first location may be identified based on a user input from a physician 24 to the workstation 55 and/or based on instructions stored in memory of the workstation 55 to automatically identify the outlet of the inferior vena cava.

At step 804, a second location, at a desired puncture site on a fossa ovalis, may be identified. The second location may be identified based on a user input from a physician 24 to the workstation 55 and/or based on instructions stored in memory of the workstation 55 to automatically identify the desired puncture site.

At step 806, a template curvature of a transseptal needle may be displayed. The template curvature may be based at least in part on a spatial relationship between the first location and the second location. The template curvature may be displayed over a predetermined needle shape similar to as illustrated in FIGS. 5A and 5B.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometries, materials, dimensions, ratios, steps, and the like discussed above are illustrative. Accordingly, the claims should not be limited to the specific details of structure and operation set forth in the written description and drawings.

The following clauses list non-limiting embodiments of the disclosure:

Clause 1. A system comprising: a processor; and non-transitory computer-readable medium with instructions thereon, that when executed by the processor, cause the system to: determine a curvature of a transseptal needle based at least in part on a spatial relationship between an access vessel and a target puncture location.

Clause 2. The system of clause 1, the access vessel comprising the inferior vena cava.

Clause 3. The system of clause 1, the access vessel comprising the superior vena cava.

Clause 4. The system of any one of clauses 1-3, the instructions further being configured to cause the system to: determine the spatial relationship between the access vessel and the target puncture location.

Clause 5. The system of any one of clauses 1-4, the instructions further being configured to cause the system to: generate an anatomical map, wherein the anatomical map comprises an access vessel approximate a right atrium and at least a portion of an interatrial septum of the right atrium; identify, based on the anatomical map, a location of the access vessel approximate the right atrium and the target puncture location; and determine the spatial relationship between the access vessel and the target puncture location.

Clause 6. The system of clause 5, wherein the spatial relationship is confirmed by intracardiac fluoroscopy and/or ultrasound data.

Clause 7. The system of clause 5 or 6, the instructions further being configured to cause the system to: generate the anatomical map based at least in part on electromagnetic mapping.

Clause 8. The system of any one of clauses 1-7, further comprising: a display, the instructions further being configured to cause the system to: display a recommended curvature of the transseptal needle on the display.

Clause 9. The system of any one of clauses 1-8, the instructions further being configured to cause the system to: receive an indication of needle selection indicating one predetermined needle shape of a plurality of predetermined needle shapes; and determine the curvature based at least in part on the indication of needle selection.

Clause 10. The system of clause 9, the instructions further being configured to cause the system to: determine a deployed position of the predetermined needle shape such that a proximal point of the predetermined needle shape is positioned at the access vessel and a distal point of the predetermined needle shape is positioned at an interatrial septum; and determine the curvature using a rotational matrix to move the distal point to the target puncture location while holding the proximal point fixed.

Clause 11. The system of clause 9 or 10, further comprising: a needle identification module configured to receive the indication of needle selection.

Clause 12. The system of clause 11, the needle identification module being configured to: receive a needle identifier from an electrically erasable programmable read-only memory (EEPROM) of a needle in communication with the system; and determine the indication of needle selection based at least in part on the needle identifier.

Clause 13. The system of any one of clauses 1-12, the instructions further being configured to cause the system to: select, based at least in part on the curvature of the transseptal needle, a preferred needle shape from a plurality of pre-determined needle shapes.

Clause 14. The system of clause 13, the instructions further being configured to cause the system to: recommend, to a user of the system, the preferred needle shape.

Clause 15. The system of any one of clauses 1-14, the instructions further being configured to cause the system to: recommend a transseptal needle design based at least in part on the curvature.

Clause 16. A method for transseptal puncture, the method comprising: identifying a first location on an anatomical map of a patient, at an outlet of an inferior vena cava; identifying a second location, on an anatomical map, at a desired puncture site on a fossa ovalis; extrapolating a curve between the first location and the second location; and providing, on the display, a needle shape template based at least in part on the extrapolated curve.

Clause 17. The method of clause 16, further comprising: determining the needle shape template based at least in part on a predetermined needle shape.

Clause 18. The method of clause 17, further comprising: determining a deployed position of the predetermined needle shape such that a proximal point of the predetermined needle shape is positioned at the first location and a distal point of the predetermined needle shape is positioned at the interatrial septum; and determining a curvature of the needle shape template using a rotational matrix to move the distal point to the desired puncture site while holding the proximal point fixed.

Clause 19. The method of any one of clauses 16-18, further comprising: recommending a predetermine needle shape.

Clause 20. A method for facilitating transseptal puncture, the method comprising: identifying, on an anatomical map, a first location at an outlet of an access vessel; identifying, on the anatomical map, a second location at a desired puncture site on the fossa ovalis; and displaying a template curvature of a transseptal needle, the template curvature being based at least in part on a spatial relationship between the first location and the second location.

What is claimed is:

1. A system comprising:
a processor; and
non-transitory computer-readable medium with instructions thereon, that when executed by the processor, cause the system to:
determine a curvature of a transseptal needle based at least in part on a spatial relationship between an access vessel and a target puncture location and a predetermined needle shape;
determine a deployed position of the predetermined needle shape such that a proximal point of the predetermined needle shape is positioned at the access vessel and a distal point of the predetermined needle shape is positioned at an interatrial septum; and
determine the curvature using a rotational matrix to move the distal point to the target puncture location while holding the proximal point fixed.

2. The system of claim 1, the access vessel comprising an inferior vena cava.

3. The system of claim 1, the access vessel comprising a superior vena cava.

4. The system of claim 1, the instructions further being configured to cause the system to:
determine the spatial relationship between the access vessel and the target puncture location.

5. The system of claim 1, the instructions further being configured to cause the system to:
generate an anatomical map, wherein the anatomical map comprises the access vessel approximate a right atrium and at least a portion of an interatrial septum of the right atrium;
identify, based on the anatomical map, a location of the access vessel approximate the right atrium and the target puncture location; and
determine the spatial relationship between the access vessel and the target puncture location.

6. The system of claim 5, the instructions further being configured to cause the system to:
modify the display of the anatomical map based on intracardiac fluoroscopy and/or ultrasound data.

7. The system of claim 5, the instructions further being configured to cause the system to:
generate the anatomical map based at least in part on electromagnetic mapping.

8. The system of claim 1, further comprising:
a display,
the instructions further being configured to cause the system to:
display a recommended curvature of the transseptal needle on the display.

9. The system of claim 1, the instructions further being configured to cause the system to:
receive an indication of a needle selection of a needle in a catalogue of needles; and
identify the predetermined needle shape based on the indication of the needle selection.

10. The system of claim 9, the instructions further being configured to cause the system to:
receive a needle identifier from an electrically erasable programmable read-only memory (EEPROM) of a needle in communication with the system; and
determine the indication of needle selection based at least in part on the needle identifier.

11. The system of claim 1, the instructions further being configured to cause the system to:
select, based at least in part on the curvature of the transseptal needle, a preferred needle shape from a plurality of pre-determined needle shapes.

12. The system of claim 11, the instructions further being configured to cause the system to:
recommend, to a user of the system, the preferred needle shape.

13. The system of claim 1, the instructions further being configured to cause the system to:

recommend a transseptal needle design based at least in part on the curvature.

14. A method for transseptal puncture, the method comprising:
- identifying a first location on an anatomical map of a patient, at an outlet of an inferior vena cava;
- identifying a second location, on the anatomical map, at a desired puncture site on a fossa ovalis;
- extrapolating a curve between the first location and the second location;
- determining a deployed position of a predetermined needle shape such that a proximal point of the predetermined needle shape is positioned at the first location and a distal point of the predetermined needle shape is positioned at an interatrial septum;
- determining a curvature of a needle shape template based at least in part on the extrapolated curve and using a rotational matrix to move the distal point to the desired puncture site while holding the proximal point fixed; and
- providing, on a display, the needle shape template.

15. The method of claim 14, further comprising:
recommending the predetermined needle shape.

* * * * *